United States Patent [19]

Summers et al.

[11] Patent Number: 4,769,387
[45] Date of Patent: Sep. 6, 1988

[54] DIBENZOFURAN LIPOXYGENASE INHIBITING COMPOUNDS, COMPOSITIONS AND USE

[75] Inventors: James B. Summers, Libertyville; Jimmie L. Moore, Gurnee, both of Ill.

[73] Assignee: Abbott Laboratories, Abbott Park, Ill.

[21] Appl. No.: 120,301

[22] Filed: Nov. 13, 1987

[51] Int. Cl.$^4$ .................... A61K 31/34; C07D 307/91
[52] U.S. Cl. ................................ 514/468; 514/314; 514/337; 546/175; 546/269; 549/461
[58] Field of Search ............... 546/175, 269; 549/461; 514/314, 337, 468

[56] References Cited

U.S. PATENT DOCUMENTS 3,657,281  4/1972  Short .................................. 549/461

Primary Examiner—Robert W. Ramsuer
Attorney, Agent, or Firm—Steven R. Crowley; Steven F. Weinstock; Martin L. Katz

[57] ABSTRACT

Compounds of the formula:

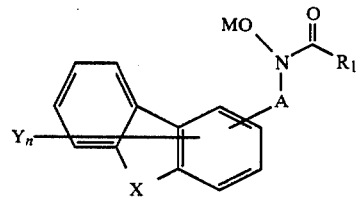

wherein $R_1$ is (1) hydrogen, (2) $C_1$ to $C_4$ alkyl, (3) $C_2$ to $C_4$ alkenyl, or (4) $NR_2R_3$, wherein $R_2$ and $R_3$ are independently selected from hydrogen, $C_1$ to $C_4$ alkyl and hydroxyl, but $R_2$ and $R_3$ are not simultaneously hydroxyl;
X is (1) oxygen, (2) sulfur, (3) $SO_2$, or (4) $NR_4$, wherein $R_4$ is (1) hydrogen, (2) $C_1$ to $C_6$ alkyl, (3) $C_1$ to $C_6$ alkoyl or (4) aroyl;
A is selected from $C_1$ to $C_6$ alkylene and $C_2$ to $C_6$ alkenylene;
n is 0–4;
Y is selected independently at each occurrence from (1) hydrogen, (2) halogen, (3) hydroxy, (4) cyano, (5) halosubstituted alkyl, (6) $C_1$ to $C_{12}$ alkyl, (7) $C_2$ to $C_{12}$ alkenyl, (8) $C_1$ to $C_{12}$ alkoxy, (9) $C_3$ to $C_8$ cycloalkyl, (10) aryl, (11) aryloxy, (12) aroyl, (13) $C_1$ to $C_{12}$ arylalkyl, (14) $C_2$ to $C_{12}$ arylalkenyl, (15) $C_1$ to $C_{12}$ arylalkoxy, (16) $C_1$ to $C_{12}$ arylthioalkoxy, and substituted derivatives fo (17) aryl, (18) aryloxy, (19) aroyl, (20) $C_1$ to $C_{12}$ arylalkyl, (21) $C_2$ to $C_{12}$ arylalkenyl, (22) $C_1$ to $C_{12}$ arylalkoxy, or (23) $C_1$ to $C_{12}$ arylthioalkoxy, wherein substituents are selected from halo, nitro, cyano, $C_1$ to $C_{12}$ alkyl, alkoxy, and halosubstituted alkyl;
and M is hydrogen, a pharmaceutically acceptable cation, aroyl, or $C_1$ to $C_{12}$, alkoyl are potent inhibitors of 5- and/or 12-lipoxygenase enzymes. Also disclosed are lipoxygenase inhibiting compositions and a method of inhibiting lipoxygenase.

9 Claims, No Drawings

DIBENZOFURAN LIPOXYGENASE INHIBITING COMPOUNDS, COMPOSITIONS AND USE

TECHNICAL FIELD

This invention relates to organic compounds which inhibit lipoxygenase enzymes. It also relates to methods and compositions for inhibiting lipoxygenase enzymes in human and animal hosts in need of such treatment.

BACKGROUND OF THE INVENTION

The lipoxygenases are a family of enzymes which catalyze the oxygenation of arachidonic acid. The enzyme 5-lipoxygenase converts arachidonic acid to 5-hydroperoxyeicosatetraenoic acid (5-HPETE). This is the first step in the metabolic pathway yielding 5-hydroxyeicosatetraenoic acid (5HETE) and the important class of mediators of inflammation, the leukotrienes (LTs).

Similarly, 12- and 15-lipoxygenase convert arachidonic acid to 12- and 15-HPETE, respectively. Biochemical reduction of 12-HPETE leads to 12-HETE, while 15-HPETE is the precursor of the class of biological agents known as the lipoxins.

A variety of biological effects are associated with these products from lipoxygenase metabolism of arachidonic acid and they have been implicated as mediators in various disease states. For example, the LTs $C_4$ and $D_4$ are potent constrictors of human airways in vitro, and aerosol administration of these substances to non-asthmatic volunteers induces broncho-constriction. $LTB_4$ and 5-HETE are potent chemotactic factors for inflammatory cells such as polymorphonuclear leukocytes. They also have been found in the synovial fluid of rheumatoid arthritic patients. Leukotrienes have also been implicated as important mediators in allergic rhinitis, psoriasis, adult respiratory distress syndrome, Crohn's disease, endotoxin shock, and ischemia induced myocardial injury among others. The biological activity of the LTs has been reviewed by Lewis and Austen (*J. Clinical Invest.* 73,889,1984 and by J. Sirois (*Adv. Lipid Res.* 21, 78, 1985).

The product 12-HETE has been found in high levels in epidermal tissue of patients with psoriasis. The lipoxins have recently been shown to stimulate elastase and superoxide ion release from neutrophils.

Thus, lipoxygenase enzymes are believed to play an important role in the biosynthesis of mediators of asthma, allergy, arthritis, psoriasis, and inflammation. Blocking these enzymes interrupts the biochemical pathways believed to be involved in these disease states.

DETAILED DESCRIPTION OF THE INVENTION

In accordance with the present invention, there are 5- and/or 12-lipoxygenase inhibiting compounds of the formula:

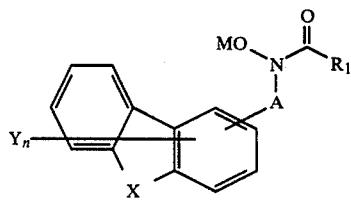

Formula I wherein $R_1$ is (1) hydrogen, (2) $C_1$ to $C_4$ alkyl, (3) $C_2$ to $C_4$ alkenyl, or (4) $NR_2R_3$ wherein $R_2$ and $R_3$ are independently selected from hydrogen, $C_1$ to $C_4$ alkyl or hydroxyl, but $R_2$ and $R_3$ are not simultaneously hydroxyl;

X is (1) oxygen, (2) sulfur, (3) $SO_2$, or (4) $NR_4$ wherein $R_4$ is (1) hydrogen, (2) $C_1$ to $C_6$ alkyl, (3) $C_1$ to $C_6$ alkoyl or (4) aroyl;

A is selected from $C_1$ to $C_6$ alkylene and $C_2$ to $C_6$ alkenylene;

Y is selected independently at each occurrence from (1) hydrogen, (2) halogen, (3) hydroxy, (4) cyano, (5) halosubstituted alkyl, (6) $C_1$ to $C_{12}$ alkyl, (7) $C_2$ to $C_{12}$ alkenyl, (8) $C_1$ to $C_{12}$ alkoxy, (9) $C_3$ to $C_8$ cycloalkyl, (10) aryl, (11) aryloxy, (12) aroyl, (13) $C_1$ to $C_{12}$ arylalkyl, (14) $C_2$ to $C_{12}$ arylalkenyl, (15) $C_1$ to $C_{12}$ arylalkoxy, (16) $C_1$ to $C_{12}$ arylthioalkoxy, and substituted derivatives of (17) aryl, (18) aryloxy, (19) aroyl, (20) $C_1$ to $C_{12}$ arylalkyl, (21) $C_2$ to $C_{12}$ arylalkenyl, (22) $C_1$ to $C_{12}$ arylalkoxy, or (23) $C_1$ to $C_{12}$ arylthioalkoxy, wherein substituents are selected from halo, nitro, cyano $C_1$ to $C_{12}$ alkyl, alkoxy, and halosubstituted alkyl; the number n is 0–4; the group(s) Y may be substituted from any of the positions on the aryl rings;

and M is hydrogen, a pharmaceutically acceptable cation, aroyl, or $C_1$ to $C_{12}$ alkoyl.

Examples of compounds which are themselves within the scope of the present invention include the following:

N-hydroxy-N-(1-dibenzofur-3-ylethyl)acetamide
N-hydroxy-N-(1-dibenzofur-3-ylethyl)urea
N-hydroxy-N-(1-dibenzofur-3-ylethyl)N'-methyl urea
N-hydroxy-N-(9-ethylcarbaz-3-ylmethyl)N40-methyl urea
N-hydroxy-N-[1-(9-ethylcarbaz-3-ylethyl)urea
N-hydroxy-N-(1-dibenzothien-3-ylethyl)urea
N-hydroxy-N-(1-dibenzofur-1-ylethyl)urea
N-hydroxy-N-(1-dibenzofur-2-ylethyl)urea
N-hydroxy-N-(1-dibenzofur-4-ylethyl)urea
N-hydroxy-N-(dibenzofur-3-ylmethyl)N'ethyl urea
N-hydroxy-N-[1-(6-nitrodibenzofur-3-yl)ethyl]N'N'-dimethyl urea
N,N'-dihydroxy-N-(1-dibenzofur-3-ylethyl)urea
N-hydroxy-N-(1-dibenzofur-3-ylethyl)formamide
N-hydroxy-N-(1-dibenzofur-3-ylethyl)butanamide
N-hydroxy-N-[1-(4-chlorodibenzofur-3-yl)ethyl]2-methylpropanamide
N-hydroxy-N-(1-dibenzofur-3-ylethyl)propenamide
N-hydroxy-N-(1-methyl-1-dibenzofur-3-ylethyl)urea
N-hydroxy-N-(2-dibenzofur-3-ylethyl)urea
N-hydroxy-N-[1-methyl-2-(8-methoxy-dibenzofur-3-yl)ethyl]urea
N-hydroxy-N-[3-(6-methoxy-dibenzofur-3-ylpropyl)urea
N-hydroxy-N-(3-dibenzofur-3-ylprop-1-yl)urea
N-hydroxy-N-(1-methyl-3-dibenzofur-3-ylprop-1-yl)urea
N-hydroxy-N-(1-dibenzocarbazol-3-ylethyl)urea
N-hydroxy-N-[1-(9-acetyl-dibenzocarbazol-3-ylethyl)urea
N-hydroxy-N-[1-(9-benzoyl-dibenzocarbazol-3-ylethyl)urea
N-hydroxy-N-(1-dibenzothien-3-ylethyl)urea 1,1-dioxide
N-hydroxy-N-[1-(6-phenyl-dibenzothien-3-yl)ethyl]urea
N-hydroxy-N-[1-(6-fluoro-dibenzofur-3-yl)ethyl]urea N-hydroxy-N-[1-(7-phenylmethyl-dibenzofur-3-yl)ethyl]urea N-hydroxy-N-[1-(5-(4-methylbenzoyl)-dibenzofur-3-yl)ethyl]urea N-hydroxy-N-[1-(6-(4-fluorophenyl)methoxy-dibenzothien-3-yl)ethyl]urea N-hydroxy-N-[1-(2-hydroxy-dibenzofur-3-yl)ethyl]urea N-hydroxy-N-(1-benzofur-3-ylethyl)urea sodium salt N-hydroxy-N-(1-dibenzothien-3-ylethyl)urea potassium salt N-hydroxy-N-(1-dibenzofur-3-ylethyl)acetamide ammonium salt N-hydroxy-N-(1-dibenzofur-3-ylethyl)urea tetrabutylammonium salt N-butyroxy-N-(1-dibenzofur-3-ylethyl)urea The term "alkylene" is used herein to mean straight or branched chain spacer radicals such as —$CH_2$—, —$CHCH_3$—, —$C(CH_3)_2$—, —$CH(C_2H_5)$—, —$CH_2CH_2$—, —$CH_2CHCH_3$—, $C(CH_3)_2C(CH_3)_2$—, $CH_2CH_2CH_2$ and the like.

The term "alkenylene" is used herein to mean straight or branched chain unsaturated spacer radicals such as —CH=CH—, —CH=$CHCH_2$—, CH=CH$CH(CH_3)$—, —C($CH_3$)=$CHCH_2$—, —$CH_2$CH=$CHCH_2$—, $C(CH_3)_2$CH=CH$C(CH_3)_2$—, and the like.

The term "alkyl" is used herein to mean straight or branched chain radicals of 1 to 12 carbon atoms, including, but not limited to methyl, ethyl, n-propyl, isopropyl, n-butyl, sec-butyl, isobutyl, tert-butyl, and the like.

The term "alkenyl" is used herein to mean straight or branched chain unsaturated radicals of 2 to 12 carbon atoms, including, but not limited to ethenyl, 1-propenyl, 2-propenyl, 2-methyl-1-propenyl, 1-butenyl, 2-butenyl, and the like.

The term "cycloalkyl" is used herein to mean cyclic radicals, preferably of 3 to 8 carbons, including, but not limited to cyclopropyl, cyclobutyl, cyclopentyl, cyclohexyl, and the like.

The term "alkoxy" is used herein to mean —$OR_5$ wherein $R_5$ is an alkyl radical, including, but not limited to methoxy, ethoxy, isopropoxy, n-butoxy, sec-butoxy, isobutoxy, tert-butoxy, and the like.

The term "alkoyl" is used herein to mean —$COR_6$ wherein $R_6$ is an alkyl radical, including, but not limited to formyl, acetyl, propionyl, butyryl, isobutyryl, pivaloyl, and the like.

The term "carboalkoxy" is used herein to mean —$COR_7$ wherein $R_7$ is an alkoxy radical, including, but not limited to carbomethoxy, carboethoxy, carboisopropoxy, carbobutoxy, carbosec-butoxy, carboisobutoxy, carbotert-butoxy, and the like.

The term "aryl" is used herein to mean substituted and unsubstituted aromatic radicals wherein the substituents are chosen from halo, nitro, cyano, $C_1$ to $C_{12}$ alkyl, alkoxy, and halo substituted alkyl, including, but not limited to phenyl, 1- or 2-naphthyl, and the like.

The term "aroyl" is used herein to mean —$COR_8$ wherein $R_8$ is an aryl radical, including, but not limited to benzoyl, 1-naphthoyl, 2-naphthoyl, and the like.

The term "aryloxy" is used herein to mean —$OR_9$ wherein $R_9$ is an aryl radical, including, but not limited to phenoxy, 1-naphthoxy, 2-naphthoxy and the like.

The term "arylalkoxy" is used herein to mean —$OR_{10}$ wherein $R_{10}$ is an arylalkyl radical, including, but not limited to phenylmethoxy (i.e., benzyloxy), 4-fluorobenzyloxy, 1-phenylethoxy, 2-phenylethoxy, diphenylmethoxy, 1-naphthylmethyloxy, 2-napthylmethyloxy, 9-fluorenoxy, 2-, 3- or 4-pyridylmethoxy, 2-, 3-, 4-, 5-, 6-, 7-, 8-quinolylmethoxy and the like.

The term "arylthioalkoxy" is used herein to mean —$SR_{11}$ wherein $R_{11}$ is an arylalkyl radical, including, but not limited to phenylthiomethoxy (i.e., thiobenzyloxy), 4-fluorothiobenzyloxy, 1-phenylthioethoxy, 2-phenylthioethoxy, diphenylthiomethoxy, 1-naphthylthiomethoxy and the like.

The term "arylalkyl" is used herein to mean an aryl group appended to an alkyl radical, including, but not limited to phenylmethyl (benzyl), 1-phenylethyl, 2-phenylethyl, 1-naphthylethyl and the like.

The term "arylalkenyl" is used herein to mean an aryl group appended to an alkenyl radical, including, but not limited to phenylethenyl, 3-phenylprop-1-enyl, 3-phenylprop-2-enyl, 1-naphthylethenyl and the like.

The terms "halo" and "halogen" are used herein to mean radicals derived from the elements fluorine, chlorine, bromine, and iodine.

The term "halosubstituted alkyl" refers to an alkyl radical as described above substituted with one or more halogens, including, but not limited to chloromethyl, trifluoromethyl, 2,2,2-trichloroethyl, and the like.

The term "pharmaceutically acceptable cation" refers to non-toxic cations including but not limited to cations based on the alkali and alkaline earth metals, such as sodium lithium, potassium, magnesium, and the like, as well as nontoxic ammonium, quaternary, ammonium, and amine cations, including, but not limited to ammonium, tetramethylammonium, tetraethylammonium, methylamine, dimethylamine, trimethylamine, triethylamine, ethylamine, and the like.

The term "lipoxygenase" is used herein to mean 5- and/or 12-lipoxygenase.

The compounds of the invention inhibit lipoxygenase, which makes the compounds useful in the treatment and prevention of disease states wherein lipoxygenase may be involved, including, but not limited to, asthma, rheumatoid arthritis, gout, psoriasis, allergic rhinitis, adult respiratory distress syndrome, Crohn's disease, endotoxin shock, benign prostatic hypertorphy, inflammatory bowel disease and/or ischemia induced myocardial or brain injury.

METHOD OF TREATMENT

This invention also provides a method of inhibiting 5- and/or 12-lipoxygenase activity in a human or lower animal host in need of such treatment which method comprises administration to the human or lower animal host of a compound of the invention in a therapeutically effective amount to inhibit lipoxygenase activity in the host. This invention also provides a method of treating asthma, rheumatoid arthritis, gout, psoriasis, allergic rhinitis, adult respiratory distress syndrome, Crohn's disease, endoxtoxin shock, and/or ischemia-induced myocardial injury in a human or lower animal in need of such treatment comprising administering to the human or lower animal a therapeutically effective amount of a compound described above. Further, this invention provides a method for treatment and prevention of symptoms of the disease states mentioned above.

The compounds of the present invention may be administered orally, parenterally or topically in dosage unit formulations containing conventional nontoxic pharmaceutically acceptable carriers, adjuvants and vehicles as desired.

The term parenteral as used herein includes subcutaneous, intravenous, intraarterial injection or infusion techniques, without limitation. The term "topically" encompasses administration rectally and by inhalation spray, as well as by the more common routes of the skin and the mucous membrane of the mouth and nose.

Total daily dose of the compounds of this invention administered to a host in single or divided doses may be in amounts, for example, of from about 0.001 to about 100 mg/kg body weight daily and more usually 0.01 to 10 mg/kg/day. Dosage unit compositions may contain such amounts of such submultiples thereof as may be used to make up the daily dose. It will be understood, however, that the specific dose level for any particular patient will depend upon a variety of factors including the body weight, general health, sex, diet, time and routine of administration, rates of absorption and excretion, combination with other drugs and the severity of the particular disease being treated.

FORMULATION OF PHARMACEUTICAL COMPOSITION

This invention also provides for compositions in unit dosage form for the inhibition of 5- or 12-lipoxygenase activity in a human or lower animal host in need of such treatment, comprising a compound of this invention and one or more nontoxic pharmaceutically acceptable carriers, adjuvants or vehicles. The amount of active ingredient that may be combined with such materials to produce a single dosage form will vary depending upon various factors, as indicated above.

A variety of materials can be used as carriers, adjuvants and vehicles in the composition of this invention, as available in the pharmaceutical arts. Injectable preparations, such as oleaginous solutions, suspensions or emulsions, may be formulated according to known art, using suitable dispersing or wetting agents and suspending agents, as needed. The sterile injectable preparation may employ a nontoxic parenterally acceptable diluent or solvent as, for example, sterile nonpyrogenic water or 1,3-butanediol. Among the other acceptable vehicles and solvents that may be employed are 5% dextrose injection, Ringer's injection and isotonic sodium chloride injection (as described in the USP/NF). In addition, sterile, fixed oils are conventionally employed as solvents or suspending media. For this purpose any bland fixed oil may be used, including synthetic mono-, di- or triglycerides. Fatty acids such as oleic acid can also be used in the preparation of injectable compositions.

Suppositories for rectal administration of the compound of this invention can be prepared by mixing the drug with suitable nonirritating excipient such as cocoa butter and polyethylene glycols, which are solid at ordinary temperatures but liquid at body temperature and which therefore melt in the rectum and release the drug.

Solid dosage forms for oral administration include capsules, tablets, pills, troches, lozenges, powders and granules. In such solid dosage forms, the active compound may be admixed with at least one inert diluent such as sucrose, lactose or starch. Such dosage forms may also comprise, as is normal practice, pharmaceutical adjuvant substances, e.g., stearate lubricating agents. In the case of capsules, tablets and pills, the dosage forms may also comprise buffering agents. Solid oral preparations can also be prepared with enteric or other coatings which modulate release of the active ingredients.

Liquid dosage forms for oral administration include pharmaceutically acceptable emulsions, solutions, suspensions, syrups and elixirs containing inert nontoxic diluents commonly used in the art, such as water and alcohol. Such compositions may also comprise adjuvants, such as wetting agents, emulsifying suspending, sweetening, flavoring and perfuming agents.

SYNTHESIS OF THE COMPOUNDS

Compounds of this invention can be prepared according to the reaction sequence described in Scheme 1. Although the sequence illustrates the compound of formula I wherein $R_1$ is methyl, A is —CHCH$_3$—, X is oxygen and Y is hydrogen, it will be seen from the examples that other compounds of this invention can be prepared in the same manner using the appropriate starting materials.

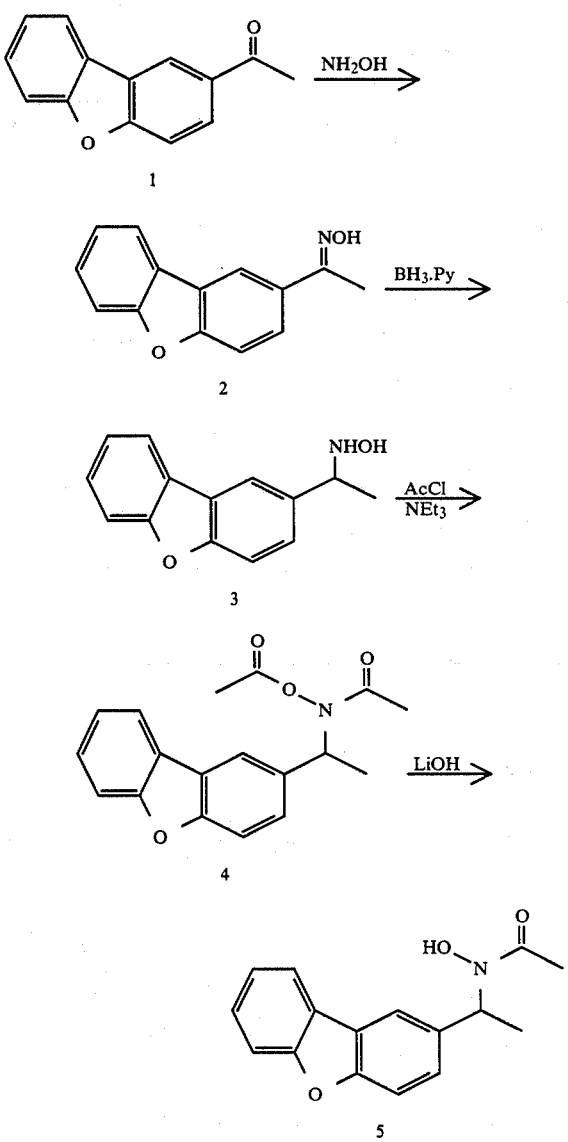

3-Acetyldibenzo[b]furan 1 is treated with hydoxyl amine in ethanol/pyridine to produce the oxime 2. This is reduced to the hydroxylamine 3 with borane pyridine complex and then converted to the N,O-diacetate 4 with acetyl chloride and triethylamine. The diacetate is converted to the hydroxamic acid 5 by hydroxylsis with lithium hydroxide.

Other reagents may also be used to carry out the same transformation. For example 2 may be converted to 3 using borane dimethyl amine, borane-tetrahydrofuran, or other borane complexes. Intermediate 2 may also be converted to 3 with sodium cyanoborohydride or with phenyldimethylsilane in trifluoroacetic acid. Hydroxylamine 3 can also be converted to 4 with acylating agents such as acetic anhydride in the presence of other bases such as pyridine.

Compounds of formula I wherein $R_1$ is $NR_4R_5$ can be prepared according to the method outlined in scheme 2, below. Although the sequence illustrates the case where $R_1$ is $NH_2$, A is —$CHCH_3$—, X is oxygen and Y is hydrogen, it will be seen from the following examples that other compounds of this invention can also be prepared in this manner.

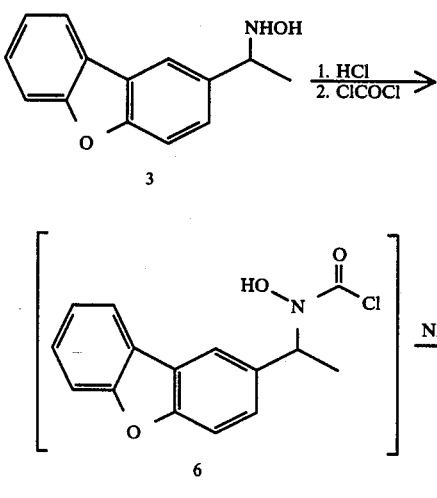

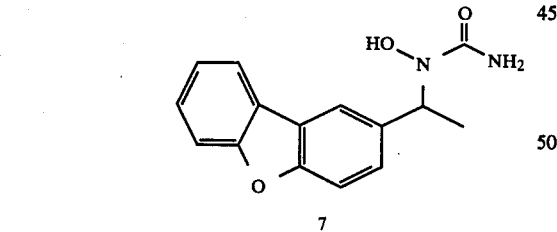

Hydroxylamine 3, the synthesis of which was described above, is treated with gaseous HCl followed by phosgene. The resulting carbamoyl chloride 6 is reacted without isolation with aqueous ammonia to yield the urea 7.

Compounds of formula I, where $R_1$ is $NR_4R_5$ and where at least one of either $R_4$ or $R_5$ is hydrogen can also be prepared according to Scheme 3, below. The sequence illustrates the case where $R_1$ is $NH_2$ (i.e., $R_4$ and $R_5$ are both hydrogen), A is —$CHCH_3$—, X is oxygen and Y is hydrogen. However, other compounds of this invention can also be prepared in this manner.

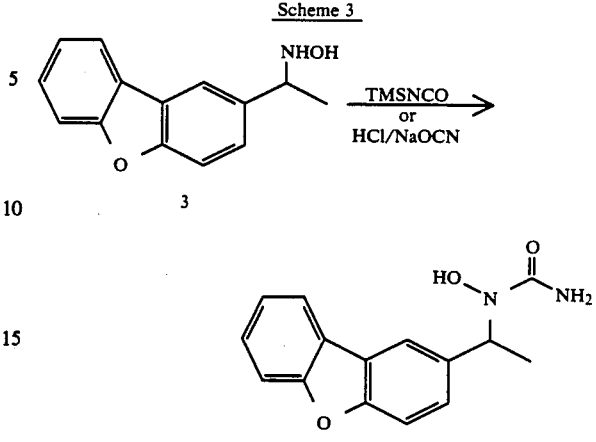

Hydroxylamine 3 is treated with trimethylsilyl isocyanate (TMSNCO), followed by ammonium chloride workup to give the urea 7. Alternatively, 3 can be treated with sodium cyanate in an acidic solution to yield the urea 7.

In addition to the methods described above, hydroxylamines such as 3 can be prepared as shown in scheme 4, below. The scheme illustrates the case where $R_1$ is methyl, A is —$CHCH_3$—, X is oxygen, and Y is hydrogen. However other compounds of this invention can also be prepared in this manner.

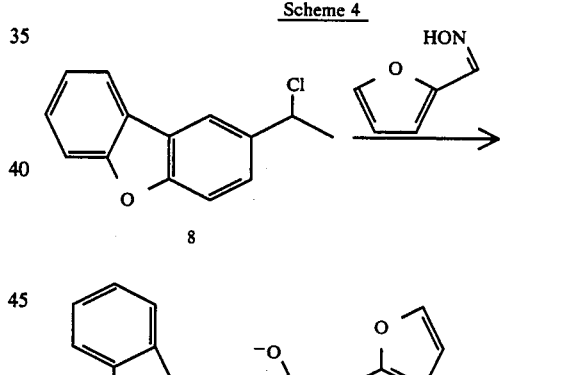

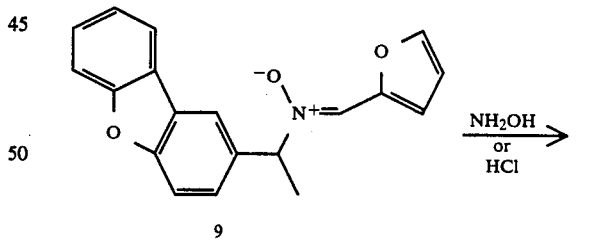

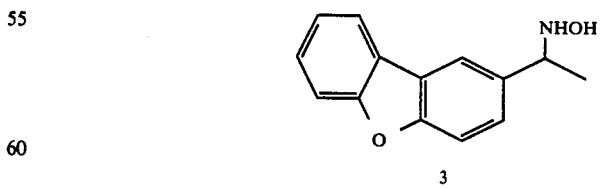

Chloride 8 is treated with Z-furfuraldehyde oxime and a base such as sodium methoxide to give nitrone 9. The nitrone is then hydolyzed under acidic conditions or with hydroxylamine. The hydroxyl amine can be converted to compounds such as 5 and 7 using the methodology described above. Compounds with other leaving groups such as bromides, iodides, tosylates, mesylates, triflates can be instead of chloride 8.

In addition to the methods described above compounds of this invention may also be prepared as described in scheme 5, below. the scheme illustrates the case where $R_1$ is methyl, A is —CHCH$_3$—, X is oxygen, and Y is hydrogen. However other compounds of this invention can also be prepared in this manner.

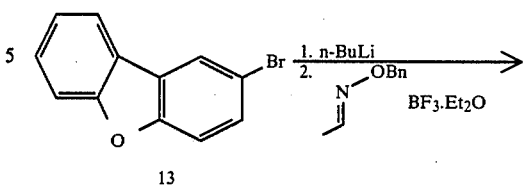

Scheme 6

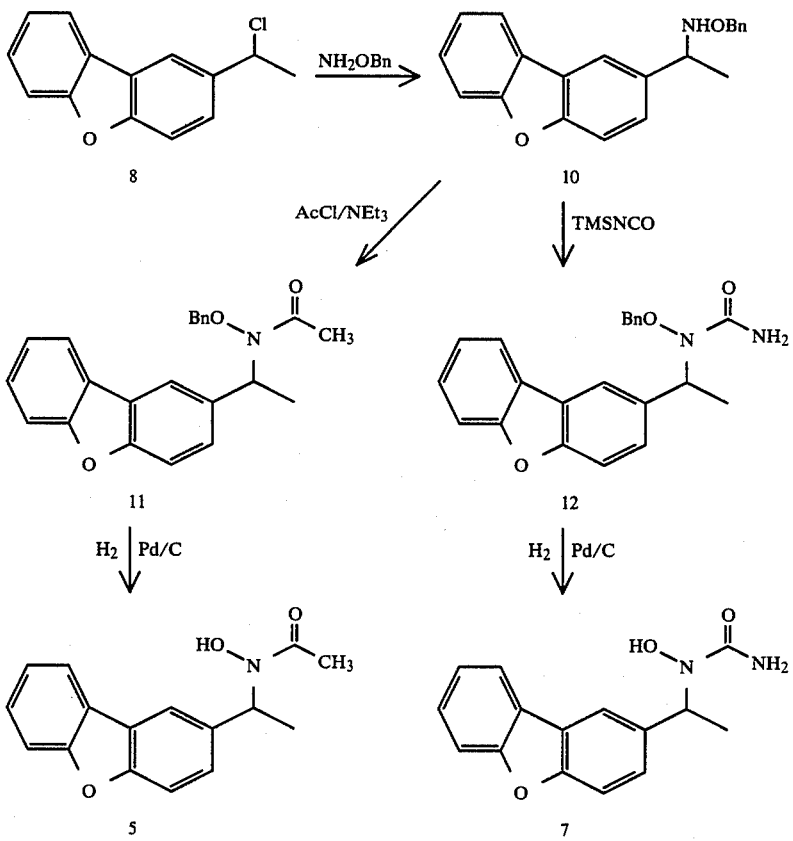

Scheme 5

Chloride 8 is heated with O-benzylhydroxylamine in a solvent such as dimethylsulfoxide or tetrahydrofuran to yield the new hydroxylamine 10. This can either be reacted with acetyl chloride as in scheme 1 to yield 11 or with trimethylsilyl isocyanate as in scheme 3 to yield 12. Compounds 11 and 12 are then hydrogenated to yield 5 to 7 respectively. Other O-protected hydroxylamines may also be used in place of O-benzylhydroxylamine such as O-tetrahydropyranyl hydroxylamine. Further other methods maybe used to convert 10 to 7, such as treatment with phosgene followed by ammonium hydroxide such as described in scheme 2, or treatment with sodium cyanate Compounds of this invention in which A is —CH$_2$— or —CH(alkyl)— may also be prepared as described in scheme 6. This scheme illustrates the synthesis of intermediate hydroxylamine 10 but other compounds of this invention can also be using

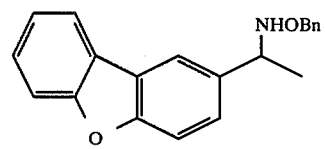

Bromide 13 is converted to 3-lithio dibenzofuran by treatment with n-butylithium. This is then treated with the O-benzyloxime of acetaldehyde in the presence of BF$_3$.Et$_2$O to give O-benzylhydroxylamine 10. This may be converted to the compounds such as 5 or 7 as described in scheme 4. Other O-protected oximes may be substituted for the O-benzyl oxime and other Lewis acids such as CeCl$_3$ may be used.

The following examples further illustrate the synthesis and use of compounds of this invention. The appropriate designations for $R_1$, A, X, and Y as defined by formula I are given for each example below.

EXAMPLE 1

N-hydroxy-N-(1-dibenzofur-3-ylethyl)acetamide a.

3-Acetyldibenzofuran

To a magnetically stirred solution of aluminum chloride (40 g, 300 mmole) in nitroethane (220 mL) under dry nitrogen was added acetyl chloride (9.5 g, 120 mmole) at 0°–5° C. The solution was stirred for 15 min, then dibenzofuran (16.8 g, 100 mmole) was added slowly and the reaction turned deep yellow-green. After 45 min at 0°, the yellow-green suspension was added to a mixture of ice and 3N HCl. The mixture was extracted with ether (2×300 mL) and extracts were dried ($Na_2SO_4$), filtered and concentrated. The crude ketone, a light amber oil, was judged to be sufficiently pure by thin layer chromatography (TLC) to use b.

3-Acetyldibenzofuran oxime

The crude ketone prepared as described in step a, was dissolved i pyridine (50 mL) and ethanol (50 mL) and hydroxylamine hydrochloride was added. The mixture was stirred overnight at ambient temperature. The reaction was concentrated and the residue was partitioned between ethyl acetate (300 mL) and 3N HCl. The ethyl acetate layer was dried ($Na_2SO_4$), filtered and concentrated in vacuo to give a crystalline residue. The crystals were rinsed with hexane, filtered and dried to give 12.3 g of the desired product, mp 132°–135° C.

c.

1-(3-Dibenzofuranyl)ethyl hydroxylamine

Borane-pyridine complex (12.3 g, 133 mmole) was added to a suspension of the crude oxime (10 g, ~44 mmole), prepared as in step b, in ethanol (50 mL). Thirty minutes later 6N HCl (30 mL) was added slowly. After being stirred overnight the reaction was concentrated in vacuo and ice was added followed by 4N NaOH. The gummy precipitate was extracted with ethyl acetate (2×150 mL) and the extracts were combined, dried over $Na_2SO_4$ and concentrated to give crude hydroxyl amine. This was carried on without further d.

N-acetoxy-N-(1-dibenzofur-3ylethyl)acetamide

Acetic anhydride (9.0 mL) was added to a solution of the crude hydroxylamine, prepared as in step c, and triethyl amine (12.4 mL) in methylene chloride (50 mL). The reaction was stirred overnight, then washed with cold water and 3N HCl. The methylene chloride layer was dried ($Na_2SO_4$) and concentrated to give a yellowish oil. This residue was chromatographed on 100 g of silica gel, eluting with 20% ethyl acetate in hexanes to give the desired product.

e.

N-hydroxy-N-(1-dibenzofur-3-ylethyl) acetamide

Lithium hydroxide mono hydrate (0.910 g, 21.7 mmole) in water (15 mL) was added to a solution of the material prepared as described in step d, (3.39 g, 10.9 mmole) in ethanol. After stirring for 30 minutes the solution was concentrated in vacuo. The residue was carefully acidified with 6N HCl, then extracted with ethyl acetate (3×200 mL). The extracts were dried ($Na_2SO_4$) filtered and concentrated. The residue was triturated with ether and filtered to give 2.03 g of the desired material as white crystals. ($R_1=CH_3$, $A=3—CHCH_3—$, $X=O$, $Y=H$)

Melting Point: 125°–127° C.

NMR (300 MHz, DMSO-$d_6$): 1.54, 1.56 (d, 3H, J=7.0); 2.03, 2.04 (s, 3H); 5.81 (m, 1H); 7.41 (m, 1H); 7.51 (m, 2H); 7.65 (d, 1H, J=8.5); 7.70 (d, 1H, J=8.5); 8.10 (m, 1H); 8.18 (m, 1 J=7.7); 9.60, 9.66 (s, 1H).

Mass spectrum (CI-$NH_3$): 270 (M+1)$^+$, 287 (M+$NH_4$)$^+$, 195.

Analysis ($C_{16}H_{15}NO_3$); Calculated—C: 71.36; H: 5.61, N: 5.20; Found C: 71.05; H: 5.56, N: 5.02.

EXAMPLE 2

N-hydroxy-N-(1-dibenzofur-3-ylethyl)urea

Trimethylsilyl isocyanate (1.2 mL) was added to a solution of 1-(3-dibenzofuranyl)ethyl hydroxylamine (0.88 g, 3.87 mmole), prepared as described in example 1, step c, in THF (6 mL). The mixture was heated at 60° C. for one hour and then poured into saturated $NH_4Cl$ solution. This was extracted with ethyl acetate (3×100 mL). The organic layer was concentrated in vacuo and the residue was triturated with ether to give the desired product as a white solid (0.84 g, 80%). ($R_1=NH_2$, $A=CHCH_3—$, $X=0$, $Y=H$)

Melting Point: 171°–173° C.

NMR (300 MHz, DMSO-$d_6$): 1.52 (d, 3H, J=7.0); 5.48 (q, 1, J=7.0; 6.34 (s, 2H); 7.39 (dt 1H, J=0.9, J=7.5); 7.51 (m, 2H); 7.62 (d, 1, J=8.6); 7.69 (d, 1, J32 8.2); 8.10 (d, 1H, J=1.5), 8.14 (m, 1H, J=7.3); 9.11 (s, 1H).

Mass spectrum (Cl-$NH_3$): 271 (M+1)$^+$, 288 (M+$NH_4$)$^+$, 195.

Analysis ($C_{15}H_{14}N_2O_3$): Calculated—C: 66.65, H: 5.22, N: 10.37; Found C: 66.49, H: 5.10, N: 10.29.

EXAMPLE 3

N-hydroxy-N-(1-dibenzofur-3-ylethyl)N'-methyl urea

The desired material was prepared as described in example 2, except using methyl isocyanate instead of trimethylisocyanate. ($R_1=NHCH_3$, $A=3—CHCH_3—$, $X=O$, $Y=H$)

Melting Point: 157°–159° C.

NMR (300 MHz, DMSO-$d_6$): 1.51 (d, 3H, J=7.4); 2.58 (d, 3H, J=4.4); 3.35 (s, 3H); 6.87 (q, 1H, 4.4); 7.39 (td, 1H, J=7.4, J=1.1); 7.51 (m, 2H); 7.62 (d, 1H, J=8.4); 7.68 (d, 1H, J=8.4); 7.68 (d, 1H, J=8.1); 8.10 (d, 1H, J=1.5); 8.15 (m, 1);

Mass spectrum (CI-$NH_3$): 302 (M+1)$^+$, 302 (M+1)$^+$, 285 (M+$NH_4$)$^+$, 195.

Analysis ($C_{16}H_{16}N_2O_3$): Calculated—C: 67.59; H: 5.67, N: 9.86; Found C: 67.21, H: 5.65, N: 9.80.

N-hydroxy-N-(9-ethylcarbaz-3-ylmethyl)N'-methyl urea

The desired material was prepared according to the method of example 2, except using 9-ethyl-3-carbazolecarboaldehyde instead of 3-acetyl dibenzofuran. ($R_1=NH_2$, $A=3—CH_2—$, $X=NC_2H_5$, $Y=H$)

Melting Point: 170°–172° C.

NMR (300 MHz, DMSO-$d_6$): 1.28 (t, 3H, 7.5); 2.62 (d, 3H, J=5.5); 4.42 (q, 2H, J=2.5); 4.65 (s,, 2H); 6.68 (q, 1H, J=5.59; 7.17 (m, 1H); 7.41 (m, 2H), 7.55 (m, 2H); 8.02 (m, 1H); 8.10 (m, 1H) 9.24 (s, 1H).

Mass spectrum (CI-NH$_3$): 298 (M+1)$^+$, 315 (M+NH$_4$)$^+$, 208.

Analysis (C$_{17}$H$_{19}$N$_3$O$_2$): Calculated—C: 68.67, H: 6.44, N: 14.31; Found C: 68.54, H: 6.34, N: 14.11.

EXAMPLE 5

N-hydroxy-N-[1-(9-ethylcarbaz-3-yl]ethyl]urea

The desired material was prepared according to the method of example 2, except using 9-ethyl-3-acetyl carbazole instead of 3-acetyl dibenzofuran. (R$_1$=NH$_2$, A=3—CHCH$_3$—, X=NC$_2$H$_5$, Y=H)

Melting Point: 139°–142° C. (dec).

NMR (300 MHz, DMSO-d$_6$): 1.30 (t, 3H, J=7.5); 1.53 (d, 3H); J=7.5); 4.41 (q, 2H, J=7.5); 5.49 (q, 1H, J=7.5); 6.27 (brs, 2H); 7.18 (m, 1H); 7.35–7.62 (m, 4H); 8.02–8.16 (m, 2H); 9.04 (brs, 1H).

Mass spectrum (CI-NH$_3$): 298 (M+1)$^+$, 315 (M+NH$_4$)$^+$, 222.

EXAMPLE 6

N-hydroxy-N-(1-dibenzothien-3-ylethyl)urea

The desired material is prepared according to the method of example 2, except using dibenzothiophene instead of dibenzofuran. (R$_1$=NH$_2$, A=3—CHCH$_3$—, X=S, Y=H)

Examples 7–33 are prepared in a manner generally analogous to examples 1 and 2, or schemes 1–6.

EXAMPLE 7

N-hydroxy-N-(1-dibenzofur-1-ylethyl)urea (R$_1$=NH$_2$, A=1—CHCH$_3$—, X=O, Y=H).

EXAMPLE 8

N-hydroxy-N-(1-dibenzofur-2-ylethyl)urea (R$_1$=NH$_2$, A=2—CHCH$_3$—, X=O, Y=H).

EXAMPLE 9

N-hydroxy-N-(1-dibenzofur-4-ylethyl)urea (R$_1$=NH$_2$, A=4—CHCH$_3$—, X=O, Y=H).

EXAMPLE 10

N-hydroxy-N-(dibenzofur-3-ylmethyl)N'ethyl urea (R$_1$=NHC$_2$H$_5$, A=3—CH$_2$—, X=O, Y=H).

EXAMPLE 11

N-hydroxy-N-[1-(6-nitrodibenzofur-3-yl)ethyl]N'N'-dimethyl urea (R$_1$=N(CH$_3$)$_2$, A=3—CHCH$_3$—, X=O, Y=6—NO$_2$).

EXAMPLE 12

N,N'-dihydroxy-N-(1-dibenzofur-3-ylethyl)urea (R$_1$=NHOH, A=3—CHCH$_3$—, X=O, Y=H).

EXAMPLE 13

N-hydroxy-N-(1-dibenzofur-3-ylethyl)formamide (R$_1$=H, A=3—CHCH$_3$—, X=O, Y=H).

EXAMPLE 14

N-hydroxy-N-(1-dibenzofur-3-ylethyl)butanamide (R$_1$=C$_3$H$_7$, A=3—CHCH$_3$—, X=O, Y=H).

EXAMPLE 15

N-hydroxy-N-[1-(4-chlorodibenzofur-3-yl)ethyl]2-methylpropanamide (R$_1$=CH(CH$_3$)$_2$, A=3—CHCH$_3$—, X=O, Y=4—Cl).

EXAMPLE 16

N-hydroxy-N-(1-dibenzofur-3-ylethyl)propenamide (R$_1$=CH=CH$_2$, A=3—CHCH$_3$—, X=O, Y=H).

EXAMPLE 17

N-hydroxy-N-(1-methyl-1-dibenzofur-3-ylethyl)urea (R$_1$=NH$_2$, A=3—C(CH$_3$)$_2$—, X=O, Y=H).

EXAMPLE 18

N-hydroxy-N-(2-dibenzofur-3-ylethyl)urea (R$_1$=NH$_2$, A=3—CH$_2$CH$_2$—, X=O, Y=H).

EXAMPLE 19

N-hydroxy-N-[1-methyl-2-(8-methoxy-dibenzofur-3-yl)ethyl]urea (R$_1$=NH$_2$, A=3—CH$_2$CHCH$_3$—, X=O, Y=8—CH$_3$O).

EXAMPLE 20

N-hydroxy-N-[3-(6-methoxy-dibenzofur-3-ylpropyl)urea (R$_1$=NH$_2$, A=3—CH$_2$CH$_2$CH$_2$—, X=O, Y=6—CH$_3$).

EXAMPLE 21

N-hydroxy-N-(3-dibenzofur-3-ylprop-1-yl)urea (R$_1$=NH$_2$, A=3—CH=CHCH$_2$—, X=O, Y=H).

EXAMPLE 22

N-hydroxy-N-(1-methyl-3-dibenzofur-3-ylprop-1-yl)urea (R$_1$=NH$_2$, A=3—CCH$_3$=CHCH$_2$—, X=O, Y=H).

EXAMPLE 23

N-hydroxy-N-(1-dibenzocarbazol-3-ylethyl)urea (R$_1$=NH$_2$, A=3—CHCH$_3$—, X=NH, Y=H).

EXAMPLE 24

N-hydroxy-N-[1-(9-acetyl-dibenzocarbazol-3-ylethyl)urea (R$_1$=NH$_2$, A=3—CHCH$_3$—, X=NCOCH$_3$, Y=H).

EXAMPLE 25

N-hydroxy-N-[1-(9-benzoyl-dibenzocarbazol-3-ylethyl)urea (R$_1$=NH$_2$, A=3—CHCH$_3$—, X=NCOC$_6$H$_5$, Y=H).

EXAMPLE 26

N-hydroxy-N-(1-dibenzothien-3-ylethyl)urea 1,1-dioxide (R$_1$=CH$_3$, A=3—CHCH$_3$—, X=SO$_2$, Y=H).

EXAMPLE 27

N-hydroxy-N-[1-(6-phenyl-dibenzothien-3-yl)ethyl]urea ($R_1$=$NH_2$, A=3—CHCH$_3$—, X=S, Y=6—C$_6$H$_5$).

EXAMPLE 28

N-hydroxy-N-[1-(6-fluoro-dibenzofur-3-yl)ethyl]urea ($R_1$=$NH_2$, A=3—CHCH$_3$—, X=O, Y=6—F).

EXAMPLE 29

N-hydroxy-N-[1-(7-phenylmethyl-dibenzofur-3-yl)ethyl]urea ($R_1$=$NH_2$, A=3—CHCH$_3$—, X=O, Y=-7—C$_6$H$_5$CH$_2$).

EXAMPLE 30

N-hydroxy-N-[1-(5-(4-methylbenzoyl)-dibenzofur-3-yl)ethyl]urea ($R_1$=$NH_2$, A=3—CHCH$_3$—, X=O, Y=5—(-4—CH$_3$C$_6$H$_4$)CO).

EXAMPLE 31

N-hydroxy-N-[1-(6-(4-fluorophenyl)methoxy-dibenzothien-3-yl)ethyl]urea ($R_1$=$NH_2$, A=3—CHCH$_3$—, X=S, Y=6—(-4—FC$_6$H$_4$)CH$_2$O).

EXAMPLE 32

N-hydroxy-N-[1-(2-hydroxy-dibenzofur-3-yl)ethyl]urea ($R_1$=$NH_2$, A=3—CHCH$_3$—, X=O, Y=2—OH).

EXAMPLE 33

N-hydroxy-N-[1-(5,6-dimethyl-dibenzothien-3-yl)ethyl]urea ($R_1$=$NH_2$, A=3—CHCH$_3$—, X=S, Y=5-,6—(CH$_3$)$_2$).

EXAMPLE 34

N-hydroxy-N-(1-dibenzofur-3-ylethyl)urea sodium salt

The material prepared as in example 2 is dissolved in tetrahydrofuran and one equivalent of sodium hydride is added. After hydrogen evolution ceases, hexane is added and the desired product collected by filtration. ($R_1$=$NH_2$, A=3—CHCH$_3$—, X=O, Y=H, M=Na).

EXAMPLE 35

N-hydroxy-N-(1-dibenzothien-3-ylethyl)urea potassium salt

The material prepared as in example 6 is dissolved in tetrahydrofuran and one equivalent of potassium hydride is added. After hydrogen evolution ceases, hexane is added and the desired product collected by filtration. ($R_1$=$NH_2$, A=3—CHCH$_3$—, X=S, Y=H, M=K).

EXAMPLE 36

N-hydroxy-N-(1-dibenzofur-3-ylethyl)acetamide ammonium salt

The material prepared as in example 2 is dissolved in tetrahydrofuran and ammonia is bubbled through the solution. Hexane is added and the desired product collected by filtration. ($R_1$=CH$_3$, A=3—CHCH$_3$—, X=O, Y=H, M=NH$_4$).

EXAMPLE 37

N-hydroxy-N-(1-dibenzofur-3-ylethyl)urea tetrabutylammonium salt

The material prepared as in example 2 is dissolved in tetrahydrofuran and one equivalent of tetrabutyl ammonium hydroxide is added. Hexane is added and the desired product collected by filtration. ($R_1$=$NH_2$, A=-3—CHCH$_3$—, X=O, Y=H, M=N(C$_4$H$_9$)$_4$).

EXAMPLE 38

N-butyroxy-N-(1-dibenzofur-3-ylethyl)urea

The material prepared as in example 2 and 1.1 equivalents of triethylamine are dissolved in tetrahydrofuran and 1 equivalent of butyryl chloride is added. Ether is added and the material is washed with 2N HCl, dried with MgSO$_4$ and evaporated to yield the desired product. ($R_1$=$NH_2$, A=3—CHCH$_3$—, X=O, Y=H).

EXAMPLE 39

Lipoxygenase IC50 Determination

Assays to determine 5-lipoxygenase activity were performed in 200 µL incubations containing the 20,000 xg supernatant from $6 \times 10^4$ homogenized RBL-1 cells, 2% DMSO vehicle and various concentrations of the test compound. Reactions were initiated by addition of radiolabelled arachidonic acid and terminated by acidification and ether extraction. Reaction products were separated from nonconverted substrate by thin layer chromatography and measured by liquid scintillation spectroscopy. All treatments were evaluated in triplicate incubations. Inhibition of 5-lipoxygenase activity was computed by comparison of the quantity of products formed in the treatment incubations to the mean product formation in vehicle control groups (n=8). IC$_{50}$ values and 95% confidence limits were computed by linear regression analysis of percentage inhibition versus log inhibitor concentration plots. The results of the assay indicate that the compounds are inhibitors of 5-lipoxygenase.

TABLE 1

In vitro 5-lipoxygenase inhibitory potency of compounds of this invention.

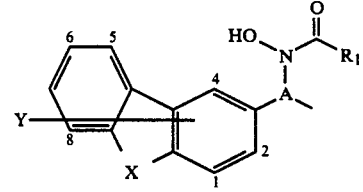

| Example | $R_1$ | A | X | Y | IC$_{50}$(µM) |
|---|---|---|---|---|---|
| 1 | CH$_3$ | CHCH$_3$ | O | H | 0.29 |
| 2 | NH$_2$ | CHCH$_3$ | O | H | 0.23 |
| 3 | NHCH$_3$ | CHCH$_3$ | O | H | 0.29 |
| 4 | NH$_2$ | CH$_2$ | NC$_2$H$_5$ | H | 0.39 |
| 5 | NH$_2$ | CHCH$_3$ | NC$_2$H$_5$ | H | 0.38 |

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

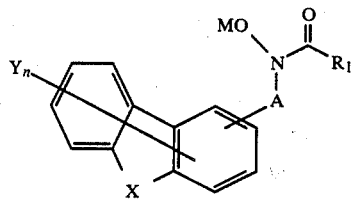

wherein $R_1$ is (1) hydrogen, (2) $C_1$ to $C_4$ alkyl, (3) $C_2$ to $C_4$ alkenyl, or (4) $NR_2R_3$, wherein $R_2$ and $R_3$ are independently selected from hydrogen, $C_1$ to $C_4$ alkyl and hydroxyl, but $R_2$ and $R_3$ are not simultaneously hydroxyl;

X is oxygen,

A is selected from $C_1$ to $C_6$ alkylene and $C_2$ to $C_6$ alkenylene;

n is 0–4;

Y is selected independently at each occurrence from halogen, hydroxy, cyano, halosubstituted alkyl, $C_1$ to $C_{12}$ alkyl, $C_2$ to $C_{12}$ alkenyl, $C_1$ to $C_{12}$ alkoxy, $C_3$ to $C_8$ cycloalkyl, aryl, aryloxy, aroyl, $C_1$ to $C_{12}$ arylalkyl, $C_2$ to $C_{12}$ arylalkenyl, $C_1$ to $C_{12}$ arylalkoxy, $C_1$ to $C_{12}$ arylthioalkoxy, and substituted derivatives of aryl, aryloxy, aroyl, $C_1$ to $C_{12}$ arylalkyl, $C_2$ to $C_{12}$ arylalkenyl, $C_1$ to $C_{12}$ arylalkoxy, or $C_1$ to $C_{12}$ arylthioalkoxy, wherein substituents are selected from halo, nitro, cyano, $C_1$ to $C_{12}$ alkyl, alkoxy, and halosubstituted alkyl;

and M is hydrogen, a pharmaceutically acceptable cation, aroyl, or $C_1$ to $C_{12}$ alkoyl.

2. A compound according to claim 1 wherein $R_1$ is $CH_3$.

3. A compound according to claim 1 wherein $R_1$ is $NH_2$.

4. A compound according to claim 1 wherein A is —$CHCH_3$—.

5. A method for inhibiting 5-and/or 12-lipoxygenase activity comprising administering to a human or lower animal in need of such treatment, a therapeutically effective amount of a compound of claim 1.

6. The method of claim 5 wherein $R_1$ is $CH_3$.

7. The method of claim 5 wherein $R_1$ is $NH_2$.

8. The method of claim 5 wherein A is —$CHCH_3$—.

9. A pharmaceutical composition for inhibiting 5- and/or 12-lipoxygenase, comprising a pharmaceutical carrier and a therapeutically effective amount of a compound of claim 1.

* * * * *